US00PP29245P3

(12) United States Plant Patent
Van Swieten

(10) Patent No.: US PP29,245 P3
(45) Date of Patent: Apr. 17, 2018

(54) ***PHALAENOPSIS* ORCHID PLANT NAMED 'PHALFOWIC'**

(50) Latin Name: *Phalaenopsis hybrid*
Varietal Denomination: PHALFOWIC

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 7 days.

(21) Appl. No.: 15/330,177

(22) Filed: Aug. 18, 2016

(65) Prior Publication Data

US 2018/0054939 P1 Feb. 22, 2018

(51) Int. Cl.
*A01H 5/02* (2018.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

UPOV-PLUTO: Plant Variety Database, citation for 'PHALFOWIC' retrieved from the Internet on Oct. 21, 2017 (1 page total).*
EU Community Plant Variety Rights Application No. 2016/0965, Application n°A201600654, filed Apr. 18, 2016, 8 pages.
EU Community Plant Variety Office Official Gazette, 3.2016, Jun. 15, 2016, cover page and pp. 35, 52.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALFOWIC', particularly characterized by having very white, large flowers, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALFOWIC'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFOWIC'.

The new *Phalaenopsis* plant is a product of a planned breeding program conducted by the inventor in Bleiswijk, The Netherlands. The objective of this breeding program was to create a new *Phalaenopsis* plant with numerous attractive and large, very white flowers, suitable for potted plant production.

The new *Phalaenopsis* plant 'PHALFOWIC' is a result of cross-pollination made by the inventor in February 2007 in Bleiswijk, The Netherlands of the proprietary female, or seed parent, *Phalaenopsis* hybrid '22480-01' (unpatented) with the proprietary male, or pollen parent, *Phalaenopsis* hybrid '01-1849' (unpatented).

The new *Phalaenopsis* was selected by the inventor as a single plant within the progeny of the stated cross-pollination in a controlled greenhouse in Bleiswijk, The Netherlands in February 2010. Asexual reproduction of the new *Phalaenopsis* plant by meristem tissue culture since 2012 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALFOWIC' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFOWIC' as a new and distinct variety of *Phalaenopsis* plant.

1) Very white, large flowers;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in July 2016. Colors in the photographs may differ from the color values cited in the detailed botanical description, which accurately describe the actual colors of the new variety.

DESCRIPTION OF THE NEW VARIETY

Figure 1:
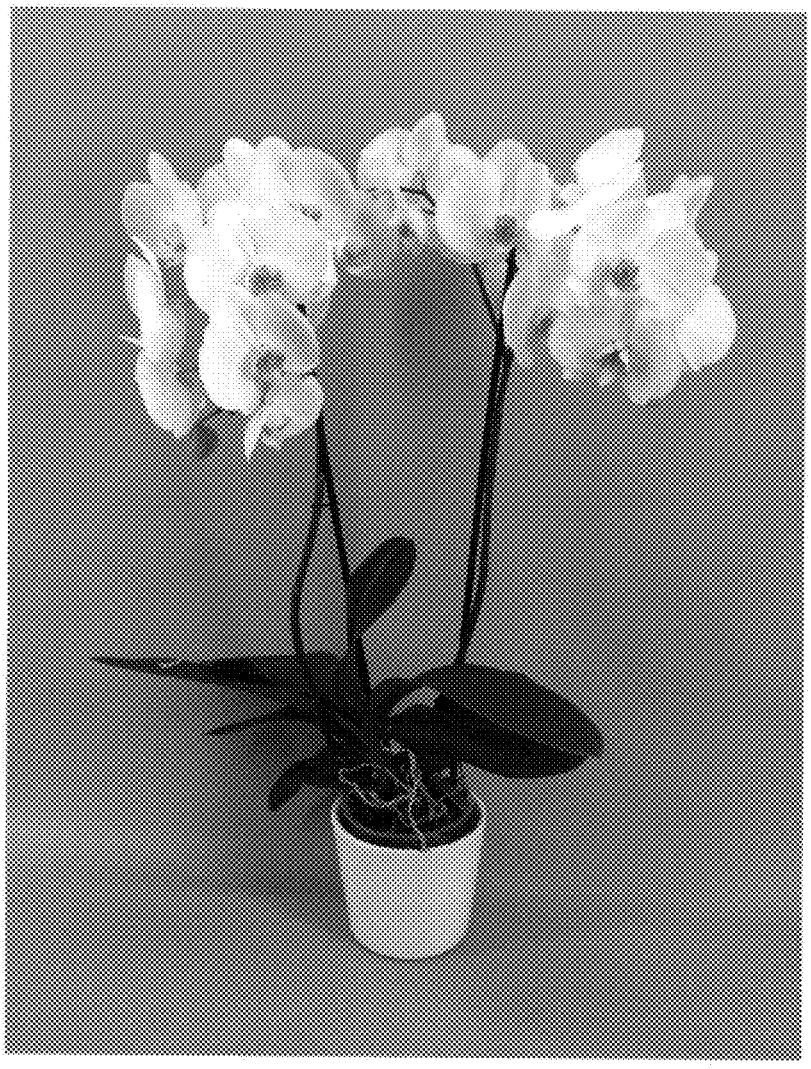
FIG. 1 shows the overall plant habit, including blooms, buds and foliage of 'PHALFOWIC'.
Figure 2:
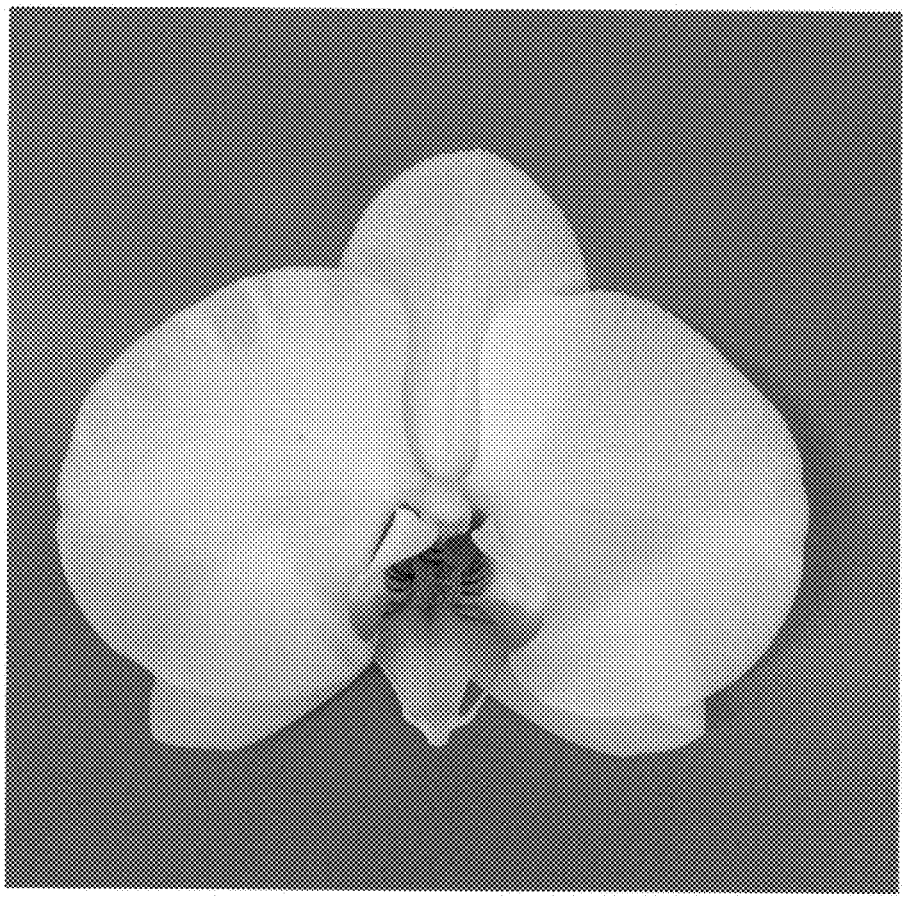
FIG. 2 shows a close-up of a flower of 'PHALFOWIC'.
Figure 3:
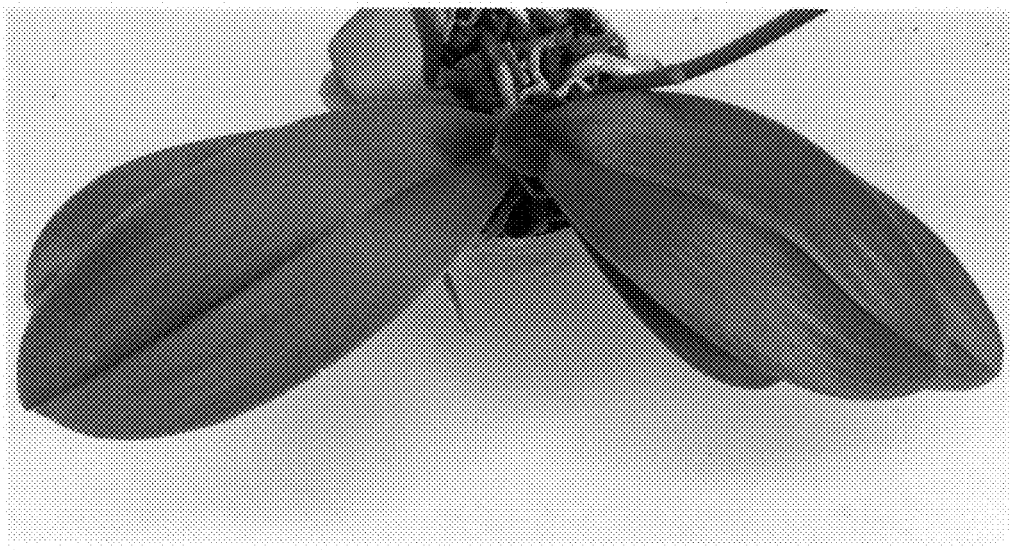
FIG. 3 shows a close-up of the leaves of 'PHALFOWIC'.

The following detailed description sets forth the distinctive characteristics of 'PHALFOWIC'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in July 2016 on 50-week old plants which were planted from a nursery tray in 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFOWIC'.

Parentage:

*Female parent*.—*Phalaenopsis* cultivar '22480-01' (unpatented).

*Male parent*.—*Phalaenopsis* cultivar '01-1849' (unpatented).

Propagation:

*Type*.—Meristem tissue culture.

Roots:

*Root description*.—Greyed-green colored roots with branching lateral roots having light purple colored root tips.

Plant:

*Commercial crop time to flowering*.—Approximately 48 to 50 weeks from a rooted cutting to finish in a 12 cm pot.

*Growth habit of peduncle*.—Standard, green leaves, panicle.

*Height* (*from soil level to top of inflorescence*).—Approximately 52.0 cm to 62.0 cm.

*Width* (*measured from leaf tips*).—About 36.0 cm to 40.0 cm.

*Vigor*.—Strong.

Leaves:

*Mature leaves*.—Quantity per plant: 8 to 10 leaves are produced before flowering. Length (fully expanded): 17.0 cm to 21.0 cm. Width: 7.5 cm to 8.5 cm. Shape: Oblong. Base shape: Moderately elongated. Apex: Unequal obtuse. Leaf blade angle with the petiole (measured from the horizontal position): Between 15 degrees and 30 degrees. Leaf margin: Entire. Color: Upper surface: RHS 147A. Lower surface: RHS 146A. Texture: Slightly rough. Thickness: 2.3 mm to 2.6 mm. Venation: Pattern: Parallel. Color of the midvein: Upper surface: RHS 147A. Lower surface: RHS 146A.

Peduncle:

*Quantity per plant*.—1 to 3.

*Number of flowers per peduncle*.—11 to 15.

*Length*.—52.0 cm to 62.0 cm.

*Diameter*.—6.3 mm to 6.6 mm.

*Strength*.—Strong.

*Aspect*.—Upright to pendant.

*Texture*.—Smooth.

*Color*.—Moderate olive brown (RHS N199A) at the base and green (RHS 146A) towards the inflorescence.

*Internode length*.—3.0 cm to 4.0 cm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 250.0 mm to 280.0 mm.

*Flowering time*.—First flowers can be expected 10 to 11 months after planting in a 12 cm (diameter) pot.

*Flower*.—Height: 81.0 mm to 83.0 mm. Diameter: 95.0 mm to 100.0 mm. Depth of lip: 24.0 mm to 26.0 mm.

*Flower longevity*.—On the plant: 14 to 22 weeks.

*Fragrance*.—Absent.

*Flower bud*.—Length: 29.0 mm to 31.0 mm. Width: 22.0 mm to 24.0 mm. Shape: Egg shaped. Color: Light green (RHS 145B to 145C) with a little touch of light purple (RHS 77D).

*Petals*.—Arrangement: Open/free. Shape: Semi-circular. Apex: Rounded asymmetric. Margin: Slightly undulated. Length (from base to tip): 46.0 mm to 48.0 mm. Width: 60.0 mm to 62.0 mm. Color (when fully opened): Upper surface: Basic color: White (RHS NN155C). Over color: Absent. Lower surface: Basic color: White (RHS NN155C). Over color: Absent.

*Dorsal sepal*.—Shape: Elliptic. Apex: Obtuse symmetric. Margin: Entire. Length (from base to tip): 47.0 mm to 49.0 mm. Width: 35.0 mm to 37.0 mm.

*Color* (*when fully opened*).—Upper surface: Basic color: White (RHS NN155C). Over color: Absent. Lower surface: Basic color: White (RHS NN155C). Over color: Light purple, fading after opening (RHS 76C).

*Lateral sepals*.—Shape: Ovate. Apex: Obtuse asymmetric. Margin: Entire. Length (from base to tip): 47.0 mm to 49.0 mm. Width: 29.0 mm to 31.0 mm. Color (when fully opened): Upper surface: Basic color: White (RHS NN155C). Over color: Light green (RHS145B) at the base. Lower surface: Basic color: White (RHS NN155C). Over color: Light green (RHS 145C) at the base and slightly light purple (RHS 76C) towards the apex.

*Labellum* (*lip*).—Whiskers: Present. Length of whiskers: 21.0 mm to 23.0 mm. Color of whiskers: Greenish-yellow (RHS 5A). Pubescence on the lip: Absent.

*Lateral lobe*.—Shape: Spatulate. Margin: Undulated. Length (from base to tip): 22.0 mm to 24.0 mm. Width: 18.0 mm to 20.0 mm. Color: White (RHS NN155C) with greenish-yellow (RHS 151B) on one side and stripes at the base (RHS 175A).

*Apical lobe*.—Shape: Triangular. Margin: Entire. Length: 22.0 mm to 24.0 mm. Width: 24.0 mm to 26.0 mm. Color: White (RHS NN155C) and greenish-yellow (RHS 151B) towards the callus.

*Callus*.—Average size: Medium to large. Height: 0.6 cm to 0.8 cm. Length: 0.7 cm to 0.9 cm. Width: 0.4 cm to 0.6 cm. Color: Yellow (RHS 5A) and dotted (RHS 175A).

*Reproductive organs*.—Column: Length: 9.0 mm to 11.0 mm. Diameter: 5.9 mm to 6.1 mm. Color: White (RHS NN155C). Pollinia: Quantity: 2. Diameter: 1.2 mm to 1.4 mm. Color: Orange (RHS 24A). Ovary: Length: 10.0 mm to 12.0 mm. Diameter: 2.3 mm to 2.5 mm. Pedicel: Length: 32.0 mm to 34.0 mm. Diameter: 2.6 mm to 2.8 mm. Color: Green at the base (RHS 146D) and lighter green (RHS 157B) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis* to date.

COMPARISON WITH PARENTAL AND COMMERCIAL VARIETIES

The female parent of 'PHALFOWIC', cultivar '22480-01' (unpatented), is no longer in existence, so a meaningful comparison cannot be made.

'PHALFOWIC' differs from male parent plant '01-1849' (unpatented) by flower size, whisker length and pedicel length. 'PHALFOWIC' has smaller diameter flowers, shorter whiskers and shorter pedicels than '01-1849'.

'PHALFOWIC' is most similar to the commercial *Phalaenopsis* plants named 'PHALDIPWEQ' (U.S. Plant Pat. No. 26,466) and 'PHALZIFY' (unpatented). 'PHALFOWIC' differs from the commercial variety 'PHALDIPWEQ' in that 'PHALFOWIC' has a yellow, dotted callus, whereas 'PHALDIPWEQ' has an orange-yellow callus. Additionally, 'PHALFOWIC' has smaller flowers and shorter whiskers than 'PHALDIPWEQ'.

'PHALFOWIC' differs from the commercial variety 'PHALZIFY' in that 'PHALFOWIC' has a lateral sepal lower surface overcolor with light green at the base and light purple towards the apex, whereas 'PHALZIFY' has a lateral sepal lower surface with no overcolor. Additionally, 'PHALFOWIC' has longer whiskers and larger flowers than 'PHALZIFY'.

I claim:

1. A new and distinct variety of *Phalaenopsis* plant named 'PHALFOWIC', substantially as described and illustrated herein.

* * * * *